(12) United States Patent
Ogura et al.

(10) Patent No.: US 6,488,938 B1
(45) Date of Patent: Dec. 3, 2002

(54) POLYLACTIC ACID SCLERAL PLUG

(75) Inventors: Yuichiro Ogura, Nagoya (JP);
Noriyuki Kunou, Yawata (JP);
Atsutoshi Ota, Osaka (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/475,371

(22) Filed: Dec. 30, 1999

Related U.S. Application Data

(63) Continuation of application No. PCT/JP98/02916, filed on Jun. 30, 1998.

(30) Foreign Application Priority Data

Jul. 2, 1997 (JP) .............................. 9-176823

(51) Int. Cl.⁷ .......................... A61K 9/00; A61K 47/32; A61F 2/00
(52) U.S. Cl. ....................... 424/400; 424/428; 424/426; 424/427; 514/772.6; 514/954; 514/955
(58) Field of Search .................... 424/428, 400, 424/426, 427; 514/772.6, 954, 955

(56) References Cited

U.S. PATENT DOCUMENTS

| | | | |
|---|---|---|---|
| 5,466,233 A | | 11/1995 | Weiner et al. |
| 5,501,856 A | * | 3/1996 | Ohtori et al. ............... 424/428 |
| 5,707,643 A | * | 1/1998 | Ogura et al. ................ 424/428 |

FOREIGN PATENT DOCUMENTS

| | | |
|---|---|---|
| EP | 488401 | 6/1992 |
| EP | 654256 | 5/1995 |
| EP | 904787 | 3/1999 |
| JP | 5-17370 A | 1/1993 |
| JP | 6-312943 A | 11/1994 |

* cited by examiner

Primary Examiner—Thurman K. Page
Assistant Examiner—Blessing Fubara
(74) Attorney, Agent, or Firm—Frishauf, Holtz, Goodman & Chick, P.C.

(57) ABSTRACT

A scleral plug which releases a drug accurately in a specified amount. The scleral plug is formed from a blend of a high-molecular weight polylactic acid having a molecular weight of 40,000 or higher and a low-molecular weight polylactic acid having a molecular weight of 40,000 or lower, and contains a drug for treating or preventing a vitreoretinal disease. The high-molecular weight polylactic acid and the low-molecular weight polylactic acid are in a blending ratio of preferably 90/10 to 50/50, more preferably 90/10 to 70/30, and most preferably 80/20. The molecular weight of the high-molecular weight polylactic acid is preferably 40,000 to 200,000. The molecular weight of the low-molecular weight polylactic acid is preferably 3,000 to 40,000, and more preferably 5,000 to 20,000. The drug is, for example, an antiulcer agent, an antiviral agent, an anti-inflammatory agent, an antifungal agent or an antimicrobial.

21 Claims, 9 Drawing Sheets

POLYLACTIC ACID SCLERAL PLUG

This application is a continuation application of international application PCT/JP98/02916 filed Jun. 30, 1998 (not published in English).

TECHNICAL FIELD

The present invention relates to a scleral plug made from a novel composition with a view to treating or preventing vitreoreti disorders.

BACKGROUND ART

Intraocular diseases such as diseases of a retina or vitreous body are often intractable, and a development of an effective treatment method is eagerly desired Though ocular diseases are most generally treated by installation of drugs, the drugs are hardly delivered to the in tissues such as a retina and vitreous body, rendering the treatment of the intraocular diseases all the more difficult. An attempt was made to treat the diseases by intravenous administration or the like. However, because of a blood-aqueous barrier, it is difficult to allow the drug to be delivered to attain an effective concentration. A method is known in which the drug is directly injected into the vitreous body. However, injection of a high concentration drug all at once causes damage to intraocular tissues and, moreover, it is not practical to repeat the injection because of the danger of infection and the cumbersomeness of treatment procedure.

In view of this, a scleral plug made of a biodegradable copolymer was devised (See U.S. Pat. No. 5,107,643). The scleral plug can be easily inserted into a small incision of sclera that is formed at the time of a vitreoretinal surgery. This scleral plug is formed from a poly(lactide-co-glycolide) made of lactic acid units and glycolic acid units, containing a drug, whereby the drug is gradually released into a vitreous body by utilizing the biodegradation of the copolymer in order to treat the vitreoretinal diseases.

The scleral plug is inserted into the small scleral incision formed at the time of the vitreoretinal surgery. The scleral plug needs to be strong enough not to break or chip by manipulation with tweezers during surgery. Moreover, the scleral plug needs to have properties to release a drug gradually during the desired period of time for treatment and to be degraded in ocular tissues and absorbed in the tissues afterwards. U.S. Pat. No. 5,707,643 discloses that he scleral plug is preferred to have a molecular weight (weight-average) of the copolymer of 10,000 to 1,000,000 and proposes that lactic acid and glycolic acid are used in an appropriate copolymenzation ratio making the most of both characteristics. However, there was still room for improvement in the scleral plug made from the poly(lactide-co-glycolide) in terms of the sustained drug release. Namely, when the drug is required to be gradually released over a long period of time, a hydrolysis rate of the plug is designed to be slow. Accordingly, the resulting oligomers and monomers owing to the hydrolysis are not released out of matrix smoothly, and they are gradually accumulating in the matrix. Consequently, it is feared that the inner osmotic pressure increases gradually and the drug is released at a time accompanied by disintegration of the plug. Accordingly, it is not easy to release the drug accurately in a constant amount to the end, and improvement of the plug was required

DISCLOSURE OF THE INVENTION

As a result of precise studies of improvement of this scleral plug, the present inventors found that the above-mentioned problem can be solved by combining a high-molecular weight polylactic acid with a low-molecular weight polylactic acid in a suitable ratio and blending them.

The scleral plug is characterized by being formed from a blend of the high-molecular weight polylactic acid and the low-molecular weight polylactic acid First, the low-molecular weight polylactic acid, which is apt to be hydrolyzed, degrades in vivo gradually and begins to release a drug gradually, and the whole plug changes into porous structure gradually. Next, the high-molecular weight polylactic acid, which is hardly hydrolyzed, degrades gradually. The release of the drug can be controlled to be constant until the plug disintegrates, since the resulting oligomers and monomers owing to hydrolysis are smoothly released through the porous structure out of matrix.

The high-molecular weight polylactic acid means polylactic acid having a molecular weight (weight-average, the same definition is applied hereinafter) of 40,000 or higher. The low-molecular weight polylactic acid means polylactic acid having a molecular weight of 40,000 or lower. However, polylactic acid having a mole weight of 40,000 is not used as the high-molecular weight polylactic acid and the low-molecular weight polylactic acid at the same time. It is not particularly necessary to define the upper limit of the molecular weight of the high-molecular weigh polylactic acid, but the molecular weight is practically 1,000,000 or lower, considering a releasing period of the drug, that is, a degradation rate of the plug. The lower limit of the molecular weight of the low-molecular weight polylactic acid is not also particularly limited, but the molecular weight is practically 3,000 or higher, considering a releasing rate of the drug. The release of the drug can be controlled by appropriately selecting each molecular weight of the high-molecular weight polylactic acid and the low-molecular weight polylactic acid used, and a blending ratio thereof.

When it is necessary to release the drug over a long period of time, the scleral plug of the present invention is particularly suitably used. The releasing period can be determined mainly on the basis of the molecular weight of the high-molecular weight polylactic acid used. For example, when a high-molecular weight polylactic acid having a molecular weight of 100,000 to 200,000 is used as a major component, the releasing period can be adjusted to about half a year to one year. When a high-molecular weight polylactic acid having a molecular weight of 40,000 to 100,000 is used as a major component, the releasing period can be adjusted to about several weeks to half a year When a high-molecular weight polylactic acid having a molecular weight of 200,000 or higher is wed, the plug can have longer-term releasing persistence. The molecular weight of the high-molecular weight polylactic acid is selected considering a possible content and an effective concentration of the drug A main role of the low-molecular weight polylactic acid is to make the plug porous and to control the release amount of the drug to be constant. This effect depends on mainly a blending ratio of the low-molecular weight polylactic acid When the blending ratio of the low-molecular weight polylactic acid is too high, an initial releasing rate of the drug is high, and it is difficult to keep the release of the drug constant over a long period of time. On the contrary, when the blending ratio is too low, it is feared that the porous structure is not formed well, the resulting oligomers and the monomers owing to the hydrolysis arc not released smoothly, the plug decomposes at a time in a final stage of the release of the drugs, and the drug is also released at a time. Accordingly, the blending ratio of the high-molecular weight polylactic acid and the low-molecular weight polylactic acid is usually about 90110 to about 50150, preferably about 90/10 to about 70/30, most preferably about 80120.

The releasing period of the drug and an amount of the drug to be released are basically controlled to be constant by the molecular weight of the high-molecular weight polylactic acid and the blending ratio of the low-molecular weight polylactic acid. However, the releasing period of the drug depends on the molecular weight of the low-molecular weight polylactic acid, too. When the molecular weight of the low-molecular weight polylactic acid is decreased, the releasing rate of the drug becomes a little MO. On the contrary, when the molecular weight is increased, the releasing rate of the drug becomes a little low. Accordingly, the molecular weight of the low-molecular weight polylactic acid adjusts the releasing period finely. The molecular weight of the low-molecular weight polylactic acid can appropriately be changed depending on the desired releasing period. The molecular weight is selected usually in the range of 3,000 to 40,000, more preferably in the range of 5,000 to 20,000.

As regards physical strength, which is a requirement of the scleral plug, the molecular weight of the polymer can be 10,000 or higher. When the high-molecular weight polylactic acid having the molecular weight of 40,000 or higher is used as a major component like the present invention, the scleral plug maintains sufficient strength.

The polylactic acid can be a DL-, L- or D-form, and it is preferable to use the DL- or L-form.

The scleral plug can have essentially the same shape and size as those disclosed in U.S. Pat. No. 5,707,643, that is, a nail-like shape comprising a head portion and a shaft portion. The end of the shaft portion can be formed in an acute-angled shape.

The scleral plug is used for treatment or prevention of various vitreoretinal diseases. Examples of specific diseases are viral or bacterial infections, proliferative vitreoretinopathy accompanied by proliferation of new blood vessels or real cells, retinal hemorrhage, retinal detachment or retinoblastoma due to various causes or the like. The drug to be contained in the scleral plug is not limited and can be selected depending on the diseases. For example, for treatment of viral infections, antiviral agents such as ganciclovir are used. Doxorubicin hydrochloride, etc. are used for treating proliferative vitreoretinopathy. Content of the drug can appropriately be adjusted depending on the kinds, the necessary effective concentrations and the releasing periods of the drug, symptoms, etc. For example, the Content of ganciclovir is usually 1 to 4 mg, preferably 1.5 to 2.5 mg. The weight of the scleral plug of the present invention is about 8 to 10 mg, and the drug content is determined considering balance of a sustained release effect and an amount required for the treatment.

A plurality of the scleral plugs of the present invention can be used simultaneously. When the scleral plug becomes unable to maintain the effective concentration of the drug, it can be replaced with a new one.

Particular techniques are not required for producing the scleral plug of the present invention For example, the scleral plug is obtained by dissolving the high-molecular weight polylactic acid, the low-molecular weight polylactic acid and the drug in a certain amount of a solvent such as acetic acid, lyophilizing the solution and then forming plugs out of the obtained powder

BRIEF DESCRIPTION OF DRAWINGS

In FIG. 9, the plug has a head portion 11, a shaft 13, and a shaft end portion 12.

BEST MODE FOR CARRYING OUT THE INVENTION

Examples are shown below. These Examples are intended for better understanding the present invention but are not to limit the scope of the present invention.

EXAMPLE 1

Production of Scleral Plug

IN acetic acid (10 ml) were dissolved a high-molecular weight polylactic acid having a molecular weight of 130,000 (800 mg), a low-molecular weight polylactic acid having a molecular weight of 5,000 (200 mg) and ganciclovir (250 mg). The obtained solution was lyophilized to give fine particle powder. A portion of the fine particle powder was placed on a hot plate to form the desired scleral plug. Ganciclovir content per a piece of the obtained scleral plug (about 1 mg) is about 2 mg.

By methods similar to Example 1 is obtained a scleral plug in which molecular weight of high-molecular weight polylactic acid is 130,000, 70,000 or 40,000, molecular weight of low-molecular weight polylactic acid is 3,000, 5,000 10,000, 20,000, or 40,000 and a ration of the high-molecular weight polylactic acid/the low-molecular weight polylactic acid is 90/10, 85/25, 80/20, 75/25, 70/30, 60/40 or 50/50. A scleral plug having ganciclovir content of about 1 mg, about 2 mg, about 3 mg or about 4 mg per a piece of the scleral plug is obtained.

EXAMPLE 2

Release Test

Figure 1:
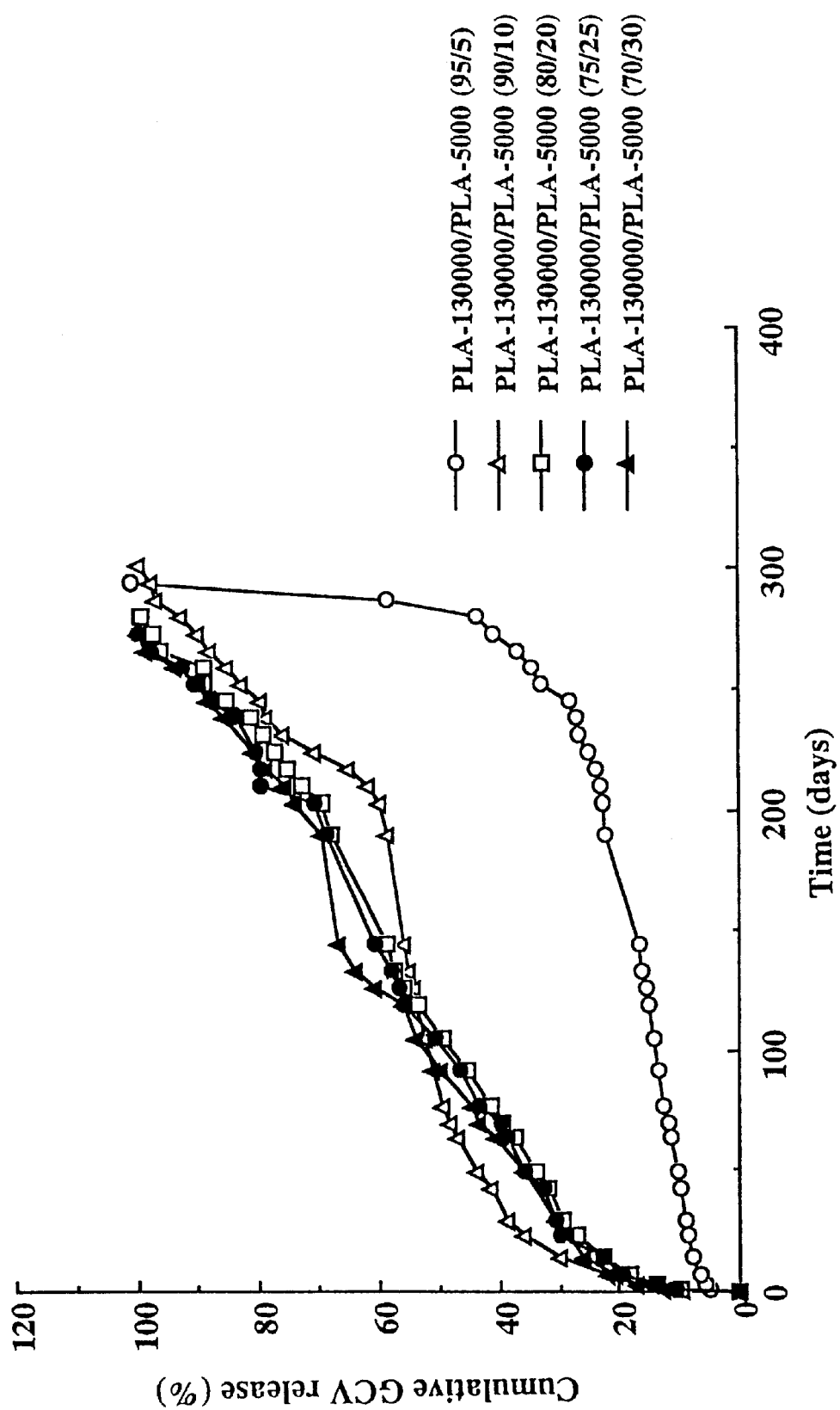
FIG. 1 is a graph showing relations between cumulative released amounts (%) of ganciclovir (GCV) from a scleral plug formed from a blend comprising high-molecular weight polylactic acid having molecular weight of 130,000 (PLA-130000) and low-molecular weight polylactic acid having molecular weight of 5,000 (PLA-5000) in a specific ratio, and a period of time (days) (average value of five samples (n=5)).
Figure 2:
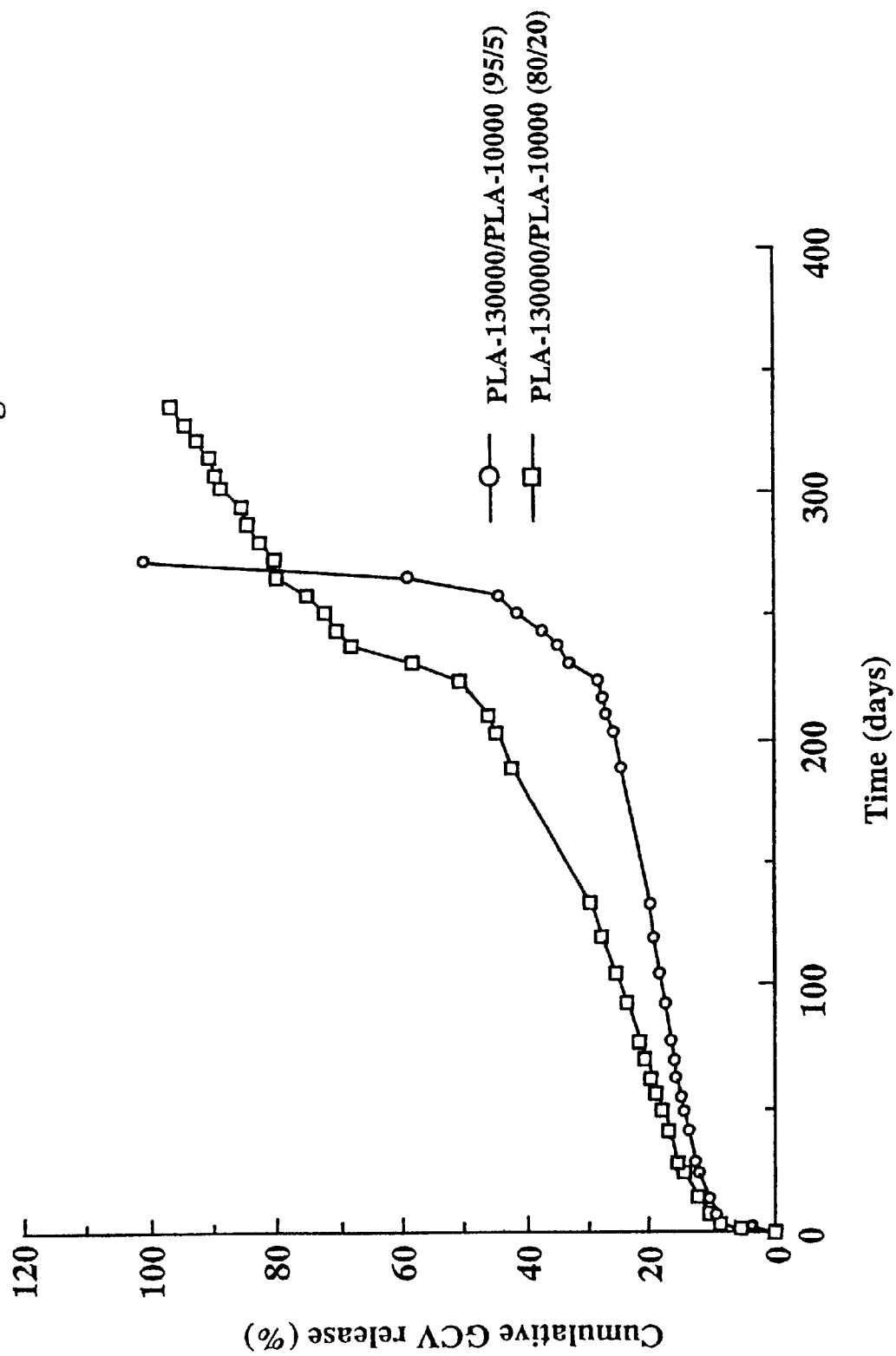
FIG. 2 is a graph showing relations between cumulative released amounts (%) of ganciclovir (GCV) from a scleral plug formed from a blend comprising high-molecular weight polylactic acid having mole weight of 130,000 (PLA-130000) and low-molecular weight polylactic acid having molecular weight of 10,000 (PLA-10000) in a specific ratio, and a period of time (days) (average value of five samples (n=5)).
Figure 3:
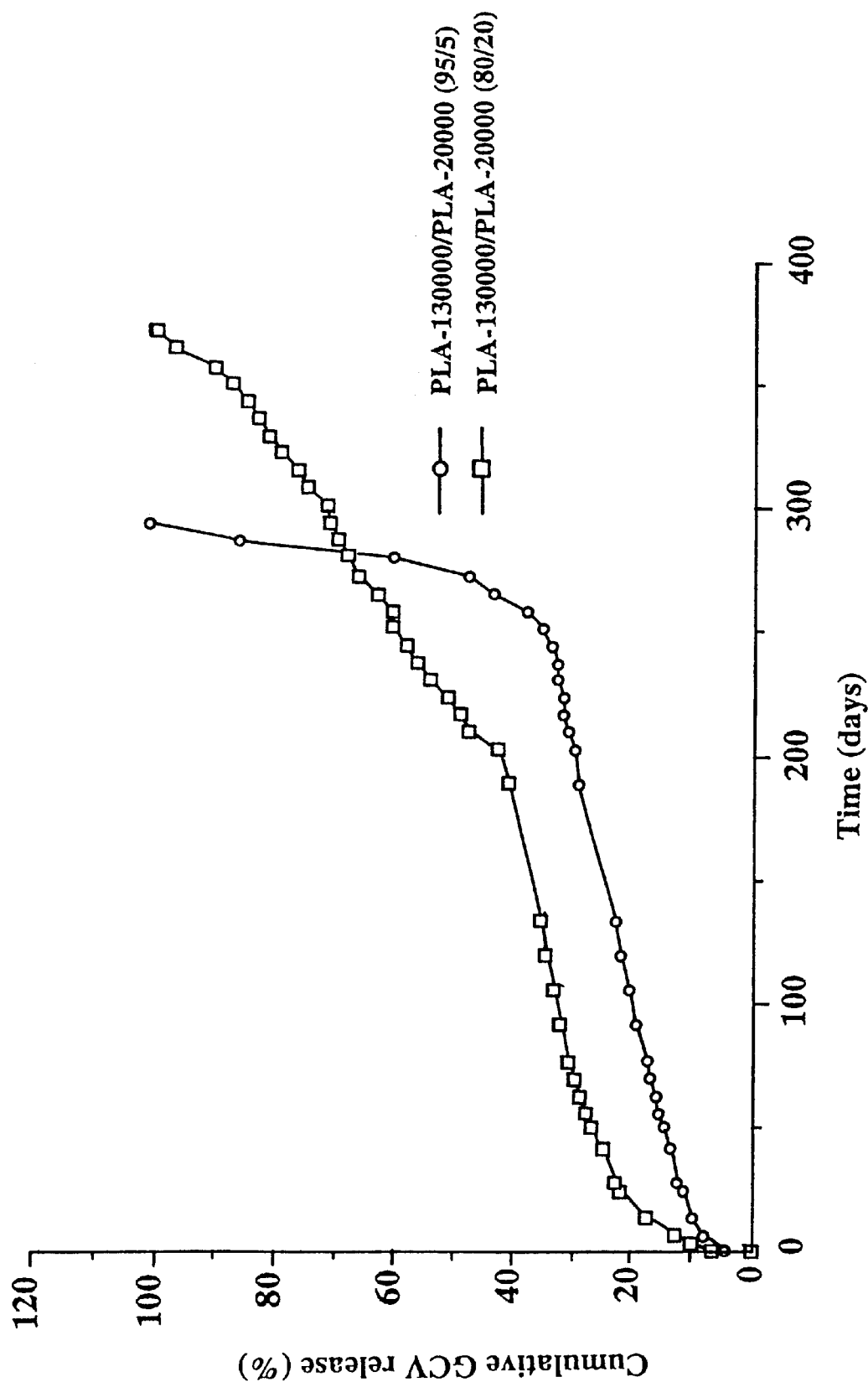
FIG. 3 is a graph showing relations between cumulative released amounts ( )of ganciclovir (GCV) from a sclera plug formed from a blend comprising high-molecular weight polylactic acid having molecular weight of 130, 000 (PLA-130000) and low-molecular weight polylactic acid having molecular weight of 20,000 (PLA-20000) in a specific ratio, and a period of time (days) (average value of five samples (n=5)).
Figure 4:
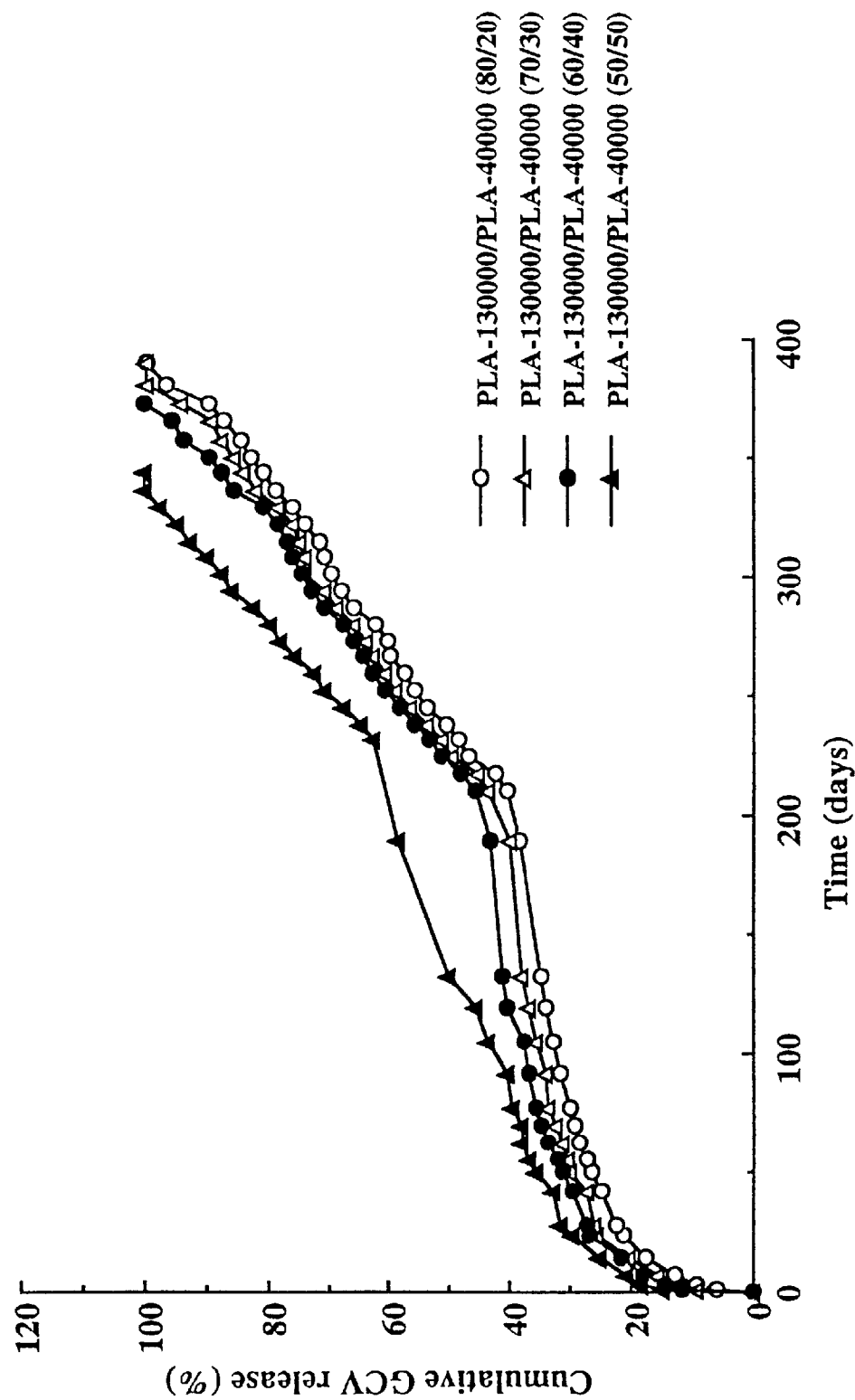
FIG. 4 is a graph showing relations between cumulative released amounts (%) of ganciclovir (GCV) from a sclera plug formed from a blend comprising high-molecular weight polylactic acid having molecular weight of 130,000 (LA-130000) and low-molecular weight polylactic acid having molecular weight of 40,000 (PLA-40000) in a specific ratio, and a period of time (days) (average value of five samples) (n=5).
Figure 5:
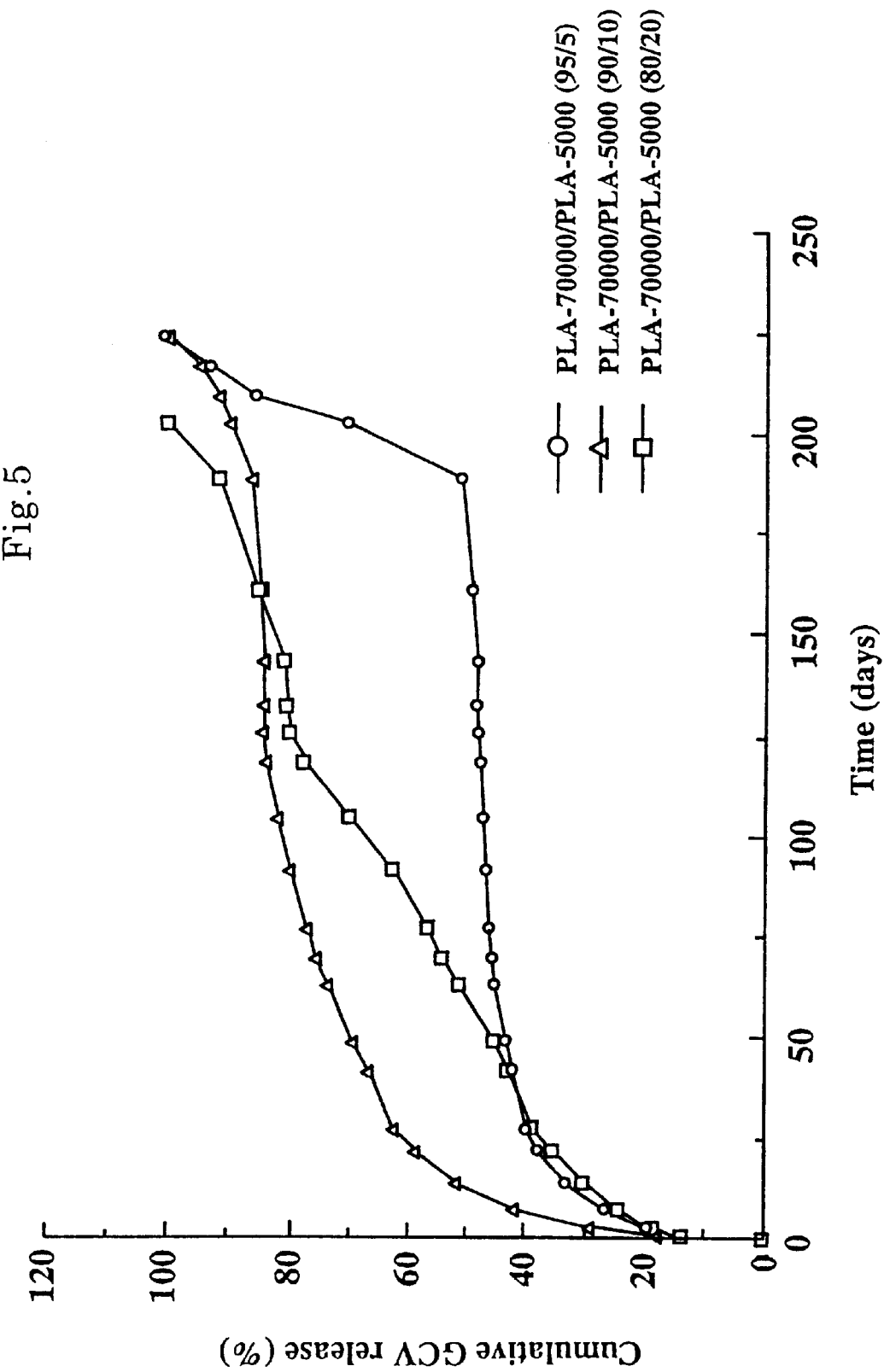
FIG. 5 is a graph showing relations between cumulative released amounts (%) of ganciclovir (GCV) from a scleral plug formed from a blend comprising high-molecular weight polylactic acid having molecular weight of 70,000 (PLA-70000)and low-molecular weight polylactic acid having molecular weight of 5,000 (PLA-5000) in a specific ration, and a period of time (day) (average value of five samples (n=5))
Figure 6:
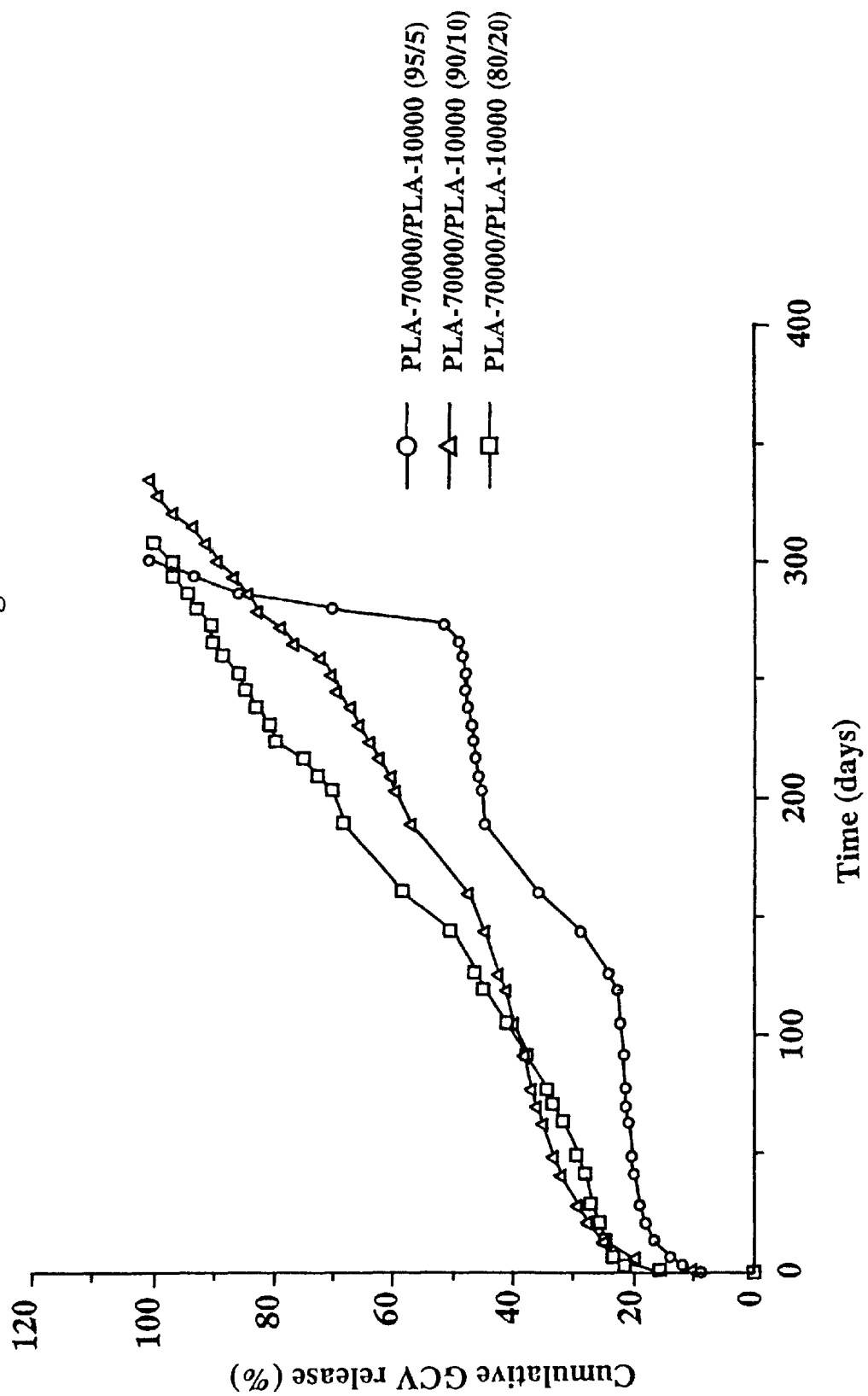
FIG. 6 is a graph showing relations between cumulative released amounts (%) of ganciclovir (GCV) from a scleral plug formed from a blend comprising high-molecular weight polylactic acid having molecular weight of 70,000 (PLA-70000) and low-molecular weight polylactic acid having molecular weight of 10,000 (PLA-10000) in a specific ratio, and a period of time (days) (average value of five samples (n=5)
Figure 7:
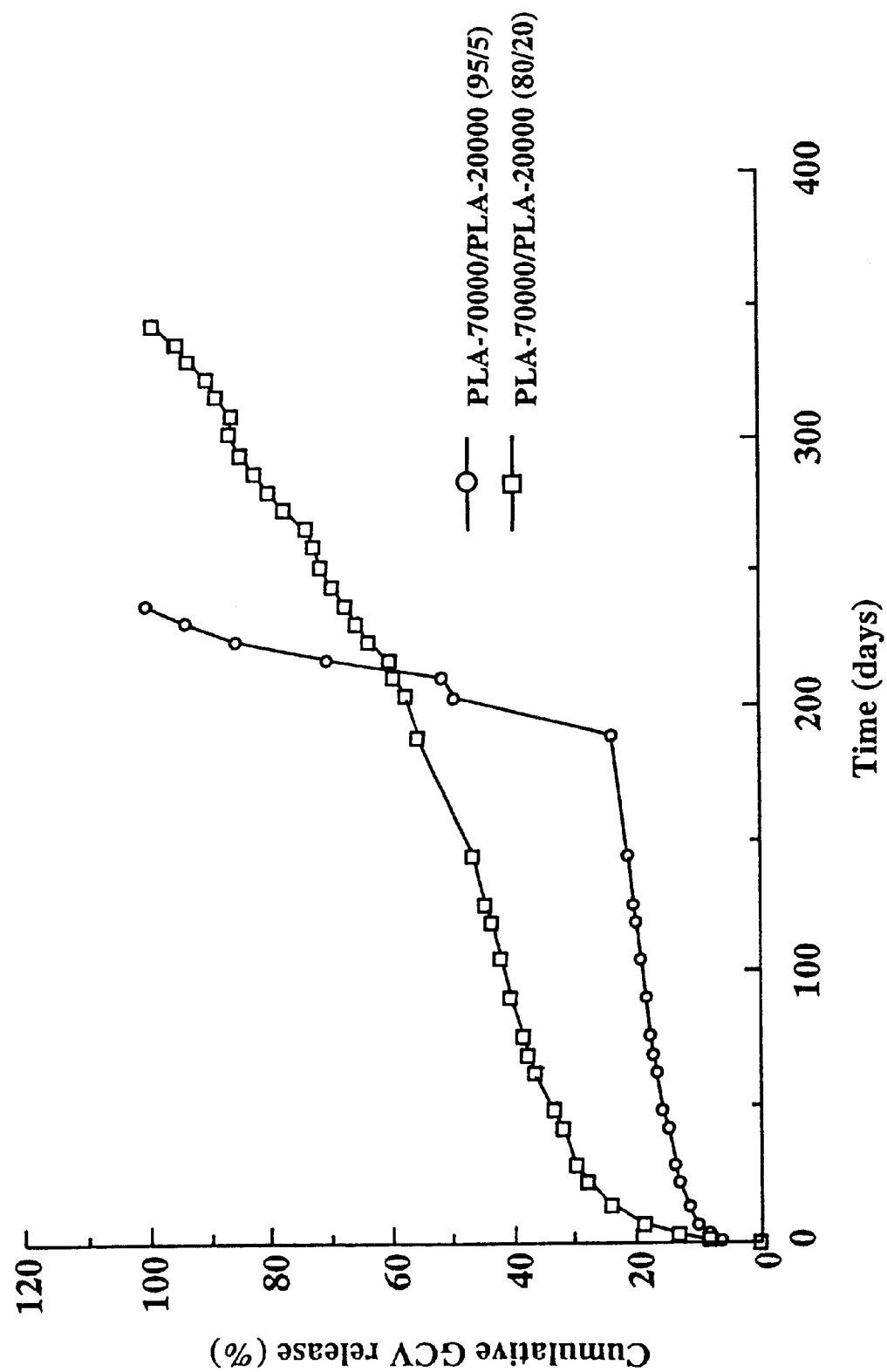
FIG. 7 is a graph showing relations between cumulative released amounts (%) of ganciclovir (GCV) from a scleral plug formed from a blend comprising high-molecular weight polylactic acid having molecular weight of 70,0000 (PLA-70000) and low-molecular weight polylactic acid having molecular weight of 20,000 (PLA-20000) in a specific ration, and a period of time (days) (average value of five samples (n=5)
Figure 8:
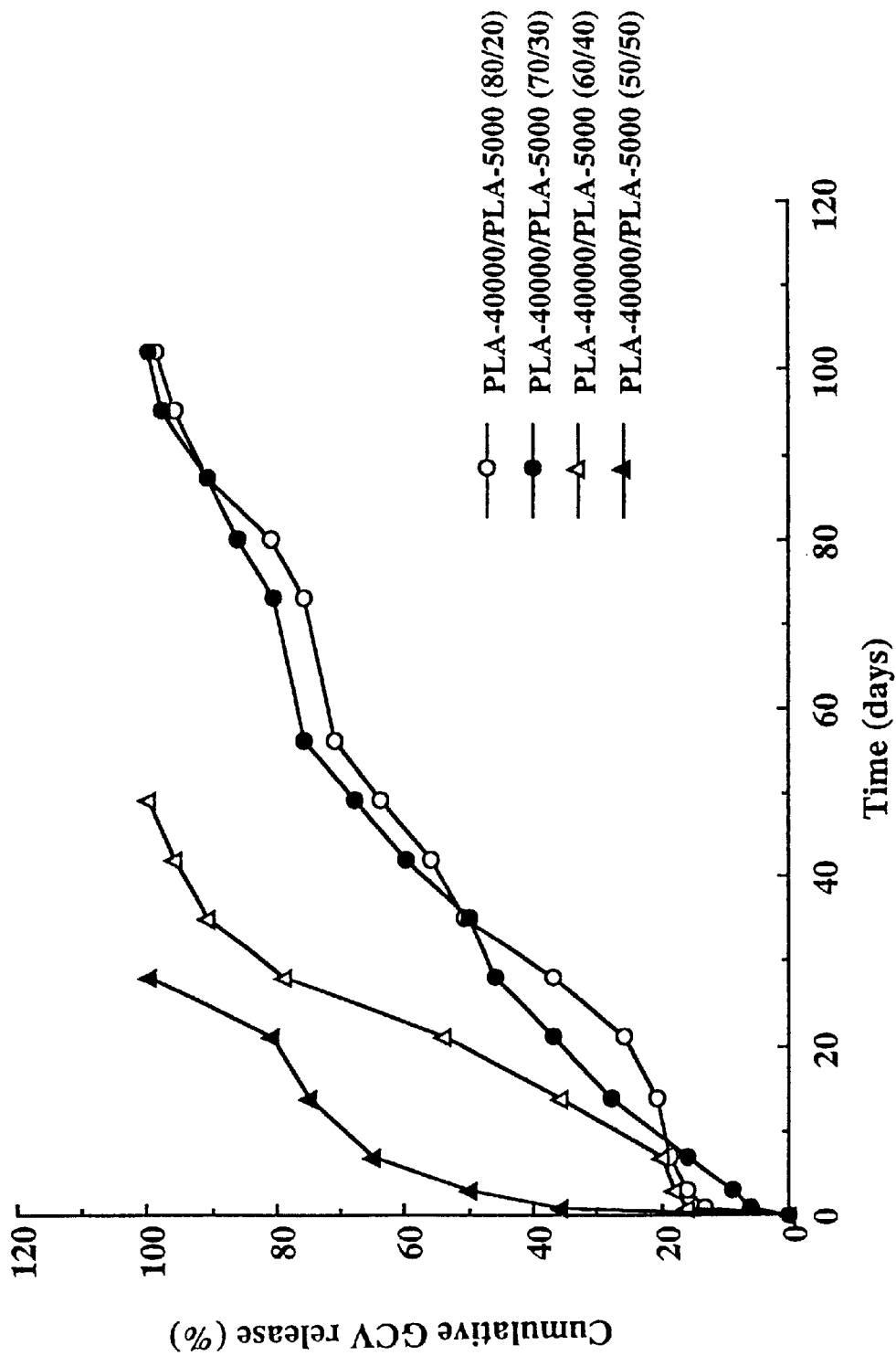
FIG. 8 is a graph showing relations between cumulative released amounts (%) of ganciclovir (GCV)from a scleral plug formed from a blend comprising high-molecular weight polylactic acid having molecular weight of 40,000 (PLA-40000) and low-molecular weight polylactic acid having molecular weight of 5,000 (PLA-5000) in a specific ratio, and a period of time (days) (average value of five samples (n=5)).
Figure 9:
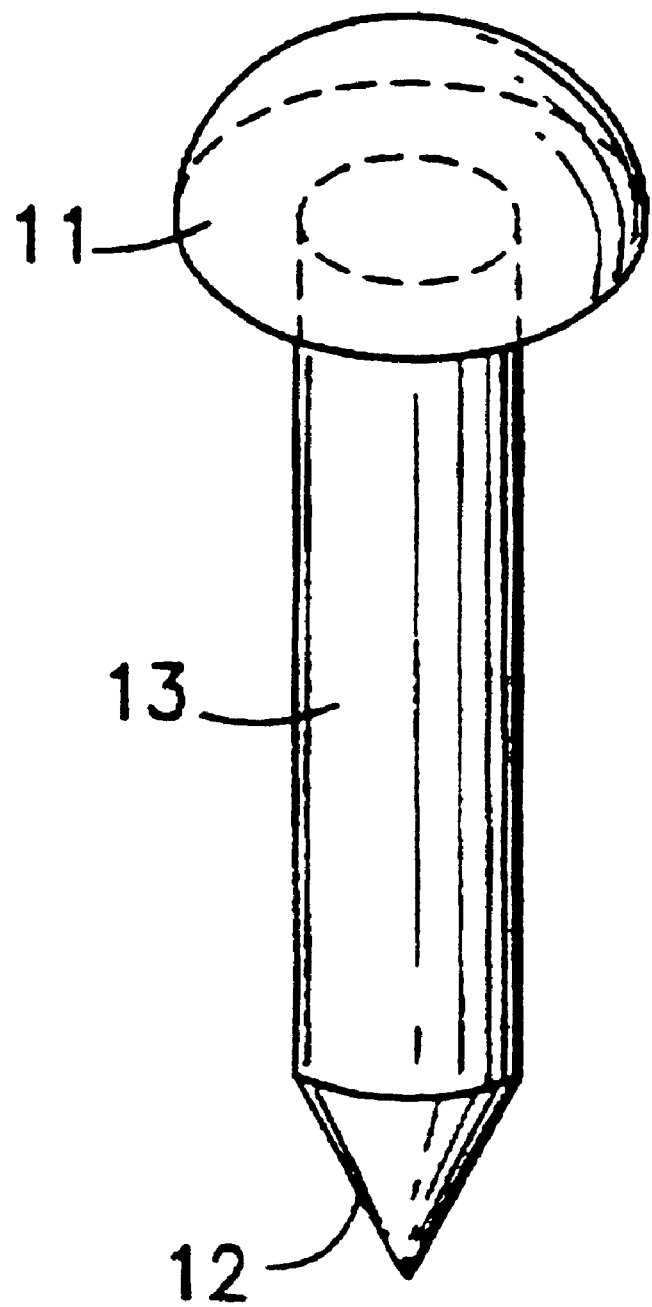
FIG. 9 is a perspective view of a scleral plug of the present invention which may be formed (including shape and dimensions) as disclosed in U.S. Pat. No. 5,707,643.

The scleral plug produced in Example 1 was shaken in a phosphate buffered solution (0.1 M, pH 7.4) to release a drug (ganciclovir). The release medium was collected at predetermined intervals and replaced with a new buffer. These operations were repeated. Absorbance of the release medium at 254 nm was measured with a spectrophotometer, and an amount of the released drug was determined. Examples of the measurement results are shown in FIGS. 1 to 8. It was confirmed that the drug (ganciclovir) does not decompose during the release test.

The results shown in FIGS. 1 to 8 teach the following.
1. Regarding Change in Blending Ratio of High-molecular Weight Polylactic Acid (HPLA) and Low-mole Weight Polylactic Acid (PLA)

1) When the blending ratio of HPLA and LPLA is 95/5, the drug is rapidly released at a latter stage of the drug release, and an amount of the released drug is not kept constant from an initial stage to the final stage of the dug release. Namely, the released amount and a period of time do not have a linear relation 2) When the blending ratio of HPLA and LPLA is 95/10 to 50/50, rapid releases of the drug hardly take place even at the latter stage of the drug release. A releasing rate of the drug is a little high at the initial stage of the drug release, but the released amount is kept almost constant from a middle stage to the find stage of the drug release. In particular, when the blending ratio is 80/20, the released amount and the period of time have an almost linear relation.
2. Regarding Effect of Molecular Weight of HPLA Comparing scleral plugs having a constant blending ratio of HPLA and LPLA and constant molecular weight of LPLA, the drug releasing period becomes longer with increasing the molecular weight of HPLA. For example, comparing FIG. 1 with FIG. 5, when the molecular weight of HPLA is 130,000, the releasing period is about 300 days When molecular weight is 70,00, the releasing period is about 200 days.
3. Regarding Effect of Molecular Weight of LPLA Comparing scleral plugs having the constant blending ratio of HPLA and LPLA and constant molecular weight of HPIA, as the molecular weight of LPLA increases, the drug releasing period becomes a little long. For example, comparing FIG. 1 with FIG. 4, when the molecular weight of LPLA is 5,000, the releasing period is about 300 days. When the molecular weight is 40,000, the releasing period is about 350 to 400 days.

Industrial Applicability

The present invention relates to a scleral plug made from a novel composition with a view to treating or preventing a retina vitreoretinal disorders.

What is claimed is:

1. A scleral plug formed from a blend comprising a high-molecular weight polylactic acid having a molecular weight of 40,000 or higher and a low-molecular weight polylactic acid having a molecular weight of 40,000 or lower, and containing a drug for treating a vitreoretinal disease, wherein the high-molecular weight polylactic acid and the low-molecular weight polylactic acid do not have a molecular weight of 40,000 at the same time.

2. The scleral plug according to claim 1, wherein the high-molecular weight polylactic acid and the low-molecular weight polylactic acid are in a blending ratio of 90/10 to 50/50.

3. The scleral plug according to claim 1, wherein the blending ratio of the high-molecular weight polylactic acid and the low-molecular weight polylactic acid is 90/10 to 70/30.

4. The scleral plug according to claim 1, wherein the blending ratio of the high-molecular weight polylactic acid and the low-molecular weight polylactic acid is 80/20.

5. The scleral plug according to claim 1, wherein the molecular weight of the high-molecular weight polylactic add is 40,000 to 200,000.

6. The scleral plug according to claim 1, wherein the molecular weight of the low-molecular weight polylactic acid is 3,000 to 40,000.

7. The scleral plug according to claim 1, wherein the molecular weight of the low-molecular weight polylactic acid is 5,000 to 20,000.

8. The scleral plug according to claim 1, wherein the drug is an antiulcer agent, an antiviral agent, an anti-inflammatory agent, an antifungal agent or an antimicrobial.

9. A scleral plug formed from a blend comprising a high-molecular weight polylactic acid having a molecular weight of 40,000 to 200,000 and a low-molecular weight polylactic acid having a molecular weight of 3,000 to 40,000, wherein the low-molecular weight polylactic acid and the high-molecular weight polylactic acid are in a blending ratio of 90/10 to 50/50, and containing a drug for treating a vitreoretinal disorder, wherein the high-molecular weight polylactic acid and the low-molecular weight polylactic acid do not each have a molecular weight of 40,000 at the same time, the scleral plug having a nail-like shape having a head portion and a shaft portion, the shaft portion having an end formed in an acute-angled shape.

10. In a method for treating a vitreoretinal disease which comprises administering a pharmaceutically effective amount of a drug effective for treating a vitreoretinal disease into a vitreous body of the eye and wherein the drug is contained in a biodegradable scleral plug having a shaft which is inserted into the vitreous body and releases said drug gradually into the vitreous body, the improvement comprising forming said shaft from a blend of a high-molecular weight polylactic acid having a molecular weight of 40,000 or higher and a low-molecular weight polylactic acid having a molecular weight of 40,000 or lower, and which contains said drug, wherein the high-molecular weight polylactic acid and the low-molecular weight polylactic acid do not each halve a molecular weight of 40,000 at the same time.

11. The method according to claim 10, wherein said shaft is formed from a blend of a high-molecular weight polylactic acid having a molecular weight of 40,000 to 200,000 and a low-molecular weight polylactic acid having a molecular weight of 3,000 to 40,000, in a blending ratio of 90/10 to 50/50, and which contains said drug.

12. The method according to claim 11 wherein said scleral plug has a nail-like shape and comprises a head portion and a shaft portion which has a tapered end.

13. The method according to claim 12, wherein the blending ratio of the high-molecular weight polylactic acid to the low-molecular weight polylactic acid is 90/10 to 70/30.

14. The method according to claim 12, wherein the blending ratio of the high-molecular weight polylactic acid to the low-molecular weight polylactic acid is 80/20.

15. The method according to claim 13, wherein the low-molecular weight polylactic acid has a molecular weight of 5,000 to 20,000.

16. The method according to claim 13, wherein the polylactic acid is in the DL-form or the L-form.

17. The method according to claim 12, wherein the drug is selected from the group consisting of ganciclovir and doxorubicin hydrochloride.

18. The method according to claim 12, wherein the drug is ganciclovir is an amount of 1 to 4 mg.

19. The method according to claim 12, wherein the drug is ganciclovir in an amount of 1.5 to 2.5 mg.

20. The method according to claim 19, wherein the scleral plug has a weight of 8 to 10 mg.

21. The scleral plug according to claim 1, wherein the scleral plug has a porous structure.

* * * * *